United States Patent [19]

Koizumi et al.

[11] Patent Number: 4,734,261
[45] Date of Patent: Mar. 29, 1988

[54] DUPLEX PIPETTE

[75] Inventors: Teruaki Koizumi; Yoshio Saito; Osamu Seshimoto, all of Asaka, Japan

[73] Assignee: Fuji Photo Film Co., Ltd., Kanagawa, Japan

[21] Appl. No.: 823,320

[22] Filed: Jan. 28, 1986

[30] Foreign Application Priority Data

Jan. 29, 1985 [JP] Japan .................................. 60-14765
Jan. 29, 1985 [JP] Japan .................................. 60-14766

[51] Int. Cl.⁴ ........................ G01N 1/14; G01N 1/16; G01N 1/26; B01L 3/02
[52] U.S. Cl. .................................. 422/100; 73/863.32; 73/863.33; 73/863.82; 73/863.84; 73/864.14; 73/864.17; 73/864.18; 73/864.25; 141/27; 141/243; 141/258; 604/191
[58] Field of Search ...................... 422/100; 73/863.31, 73/863.32, 863.33, 863.82, 863.83, 863.84, 864.01, 864.13, 864.14, 864.16, 864.17, 864.18, 864.25, 864.87; 604/191; 141/27, 258, 242, 243

[56] References Cited

U.S. PATENT DOCUMENTS

| 3,492,876 | 2/1970 | Bull et al. | 422/100 |
|---|---|---|---|
| 3,646,817 | 3/1972 | Hinchman et al. | 422/100 |
| 3,729,032 | 4/1973 | Tischlinger et al. | 141/27 |
| 3,828,980 | 8/1974 | Creighton et al. | 604/191 |
| 3,834,387 | 9/1974 | Brown | 141/27 |
| 3,853,008 | 12/1974 | Hoffa et al. | 73/863.31 |
| 4,009,611 | 3/1977 | Koffer et al. | 73/864.14 |
| 4,260,077 | 4/1981 | Schroeder | 604/191 |
| 4,459,864 | 7/1984 | Cirincione | 422/100 |

FOREIGN PATENT DOCUMENTS 6504453 10/1966 Netherlands .................... 73/863.32

Primary Examiner—Barry S. Richman
Assistant Examiner—Lynn M. Kummert
Attorney, Agent, or Firm—Jules E. Goldberg

[57] ABSTRACT

A duplex pipette comprises a housing, a pair of cylinders separately formed in the housing to extend substantially in parallel to each other, first and second piston members each having a lower end portion slidably received in one of the cylinders and a handle portion projecting outside the cylinder, and a pair of pipette tips mounted on the lower end of the housing by way of a connecting member, each of the pipette tips having a passage which communicates one of the cylinders with the outside of the housing. The connecting member is arranged so that the distance between the distal ends of the pipette tips can be changed. One of the piston members is arranged to be movable separately from the other piston member and the other piston member is arranged to be movable only together with said one piston member.

4 Claims, 10 Drawing Figures

DUPLEX PIPETTE

BACKGROUND OF THE INVENTION

1. Field of the Invention

This invention relates to a duplex pipette for taking in and letting out two kinds of liquid, and more particularly to such a duplex pipette which is advantageous for use together with an ionic activity measuring instrument.

2. Description of the Prior Art

In Japanese Unexamined Patent Publication Nos. 58(1983)-211648 and 59(1984)-30055, and Japanese Patent Application No. 59(1984)-11744, for instance, there is disclosed an ionic activity measuring instrument for potentiometrically measuring ionic activity or concentration of a specific ion contained in aqueous liquid samples such as body fluid (blood, urine, saliva and the like), liquors, city water, beverages and the like.

Generally, the ionic activity measuring instrument includes a pair of ion selective electrodes having, as the outermost layer, an ion selective layer which exhibits selective response to a specific ion. The ion selective electrodes are supported between an upper frame and a lower support frame. The upper frame is provided with a pair of liquid deposition holes each opposed to one of the ion selective electrodes and a porous bridge member (preferably, of twisted yarn) for establishing an electrical contact between a liquid sample deposited in one of the liquid deposition holes and a control liquid deposited in the other liquid deposition hole is generally mounted on the upper frame. When a plurality of ion selective electrodes are provided, a pair of porous liquid distributor members are provided between the ion selective electrode pairs and the upper frame to connect the liquid deposition holes and the ion selective electrodes.

For example, when three pairs of ion selective electrodes respectively exhibiting selective response to $Na^+$, $K^+$ and $Cl^-$ are provided, a control liquid in which the activities of these ions are known is deposited in one of the liquid deposition holes and a liquid sample in which the activities of these ions are to be detected is deposited in the other liquid deposition hole. The control liquid and the liquid sample penetrate into the corresponding porous liquid distributor members and reach the corresponding ion selective electrodes. Further, the two liquids are brought into contact with each other near the middle of the porous bridge member to establish an electrical contact. This produces a potential difference between each pair of ion selective electrodes, the value of the potential difference depending upon the difference in the activity of the corresponding ion between the liquid sample and the control liquid. By measuring the potential difference and referring to a calibration curve obtained in advance from the known activities of $Na^+$, $K^+$ and $Cl^-$ in the control liquid according to Nernst equation, the activities of these ions in the liquid sample can be known.

Such an ionic activity measuring instrument is very useful in analyzing aqueous liquid samples or in clinical analysis of liquid samples taken from the human body such as blood since the ionic activities in the liquid sample can be easily measured by depositing small amounts of the liquid sample and the control liquid.

When measuring ionic activity in a liquid sample using the ionic activity measuring instrument, it is preferred that the liquid sample and the control liquid be substantially simultaneously deposited in the liquid deposition holes. Further, in the case of measuring ionic activity in a body fluid, it is preferred that the body fluid be taken directly from the body and be deposited in one of the liquid deposition holes simultaneously with deposition, in the other liquid deposition hole, of the control liquid which is separately taken.

The liquid sample and the control liquid can be simultaneously taken in or let out by using a duplex pipette having a pair of cylinders and a pair of pistons respectively received in the cylinders. However, the distance between the liquid deposition holes of the instrument is 10 mm at most, and accordingly, if the distance between the tips of the cylinders is selected to conform to the distance between the liquid deposition holes, it will become very difficult to take in the control liquid and the liquid sample from bottles, for instance, and especially to take a liquid sample directly from a biological body. Further, it would be convenient if the two pistons can be operated either integrally or separately.

SUMMARY OF THE INVENTION

In view of the foregoing observations and description, the primary object of the present invention is to provide a duplex pipette which is very useful in depositing a liquid sample and a control liquid to the liquid deposition holes of the ionic activity measuring instrument.

Another object of the present invention is to provide a duplex pipette in which the distance between the tips of the cylinders can be changed.

Still another object of the present invention is to provide a duplex pipette in which the pistons can be operated either integrally or separately.

The duplex pipette in accordance with the present invention generally comprises a housing, a pair of cylinders separately formed in the housing to extend substantially in parallel to each other, first and second piston members each having a lower end portion slidably received in one of the cylinders and a handle portion projecting outside the cylinder, and a pair of pipette tips mounted on the lower end of the housing by way of a connecting member, each of the pipette tips having a passage which communicates one of the cylinders with the outside of the housing.

In accordance with one aspect of the present invention, the connecting member is arranged so that the distance between the distal ends of the dropping tips can be changed.

In accordance with another aspect of the present invention, one of the piston members is arranged to be movable separately from the other piston member and the other piston member is arranged to be movable only together with said one piston member.

Preferably, the pipette tips are detachably connected to the connecting member so that they can be changed for new ones, for instance.

The piston members may be actuated manually, hydraulically, pneumatically or electromagnetically.

With the duplex pipette in accordance with the present invention, the control liquid and the liquid sample can be taken in or let out either simultaneously or alternately. Generally, when the liquid sample and the control liquid are substantially equal to each other in viscosity, it is preferred that the two liquids be deposited in the liquid deposition holes of the ionic activity measuring instrument substantially simultaneously. On the other hand, when the viscosity of the liquid sample is higher than that of the control liquid, it is preferred especially in the case of the instrument having a plurality of pairs of ion selective electrodes that the liquid sample be deposited before the control liquid since the diffusing speed in the distributor member is reduced.

DESCRIPTION OF THE PREFERRED EMBODIMENTS

Figure 1:
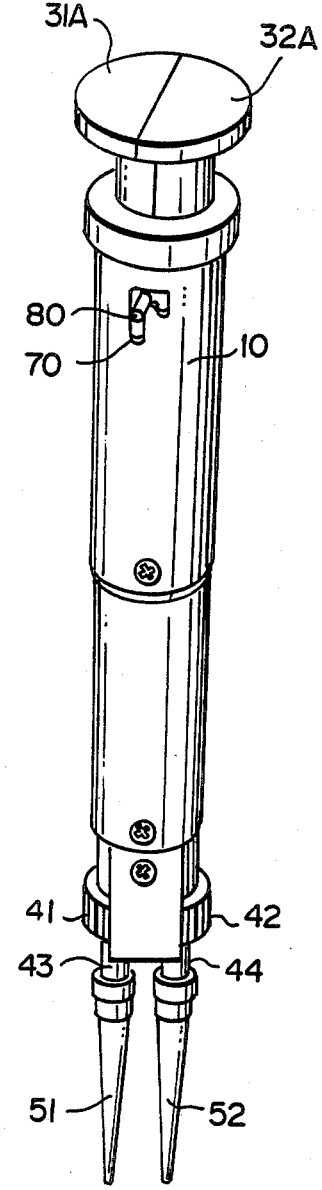
FIG. 1 is a perspective view of a duplex pipette in accordance with an embodiment of the present invention.
Figure 2:
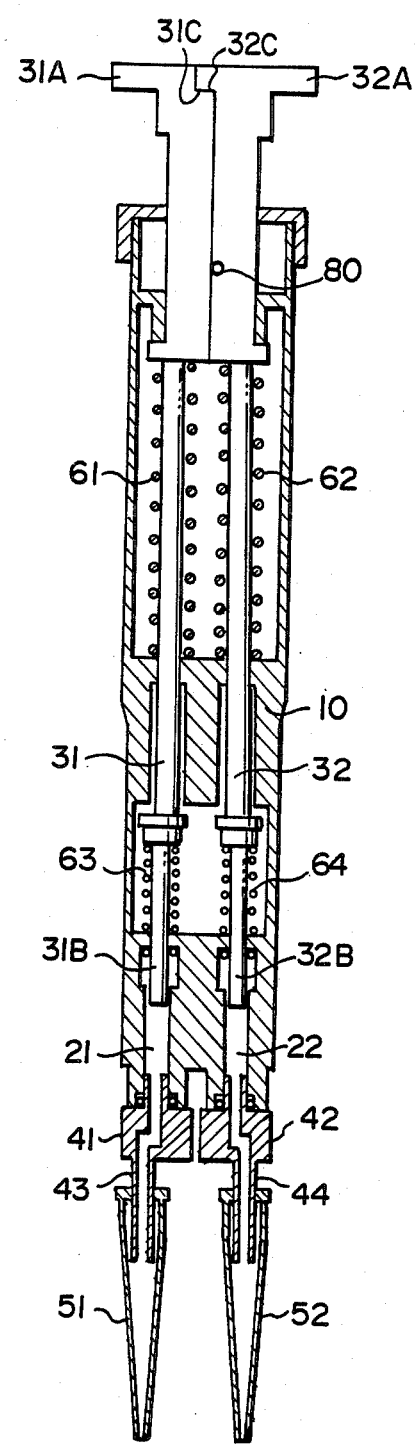
FIG. 2 is a cross-sectional view of the duplex pipette.

In FIGS. 1 and 2, a duplex pipette comprises a housing 10 having first and second cylinders 21 and 22, respectively formed in the lower portion thereof. A pair of piston members 31 and 32 extend through the housing 10 so that the upper ends 31A and 32A of the respective piston members 31 and 32 project from the upper end of the housing 10 and the lower ends 31B and 32B are respectively received in the first and second cylinders 21 and 22 for sliding motion therein. The first and second piston members 31 and 32 are resiliently supported by two pairs of coil springs 61, 62, 63 and 64 disposed in the spaces formed in the housing 10. First and second pipette tips 51 and 52 are mounted on the lower end of the housing 10 by way of first and second connecting members 41 and 42. The tips 51 and 52 have through passages respectively communicated with the first and second cylinders 21 and 22 as clearly shown in FIG. 2.

An elongated opening 70 is formed in the side wall of the housing 10 in an upper portion thereof. The opening 70 comprises two vertical portions and a horizontal portion. The vertical portions differ from each other in length and are connected with each other by the horizontal portion. A pin 80 projecting from the side surface of the second piston member 32 is slidably received in the opening 70. That is, when the pin 80 is positioned in the longer vertical portion, the second piston member 32 can be moved in the second cylinder 22 by a larger distance and when the pin 80 is positioned in the shorter vertical portions, the second member 32 can be moved only a smaller distance. Thus, the length of the stroke of the second piston member 32 can be selected. In the case of an ionic activity measuring instrument having a plurality of pairs of ion selective electrodes, a larger amount of liquid sample and control liquid is needed than in the case of an ionic activity measuring instrument having a single pair of ion selective electrodes. Thus, for example, by selecting the lengths of the two vertical portions of the opening 70 to respectively correspond to the amounts of liquids required in the instrument having three pairs of ion selective electrodes and required in the instrument having a single pair of ion selective electrodes, proper amounts of liquid sample and control liquid can be easily fed either to an instrument having a single electrode pair or to one having three electrode pairs, with the same duplex pipette.

As clearly shown in FIG. 2, the upper end portion 31A of the first piston member 31 is provided with a shoulder 31C on the side facing the second piston member 32, and the upper end portion 32A of the second piston member 32 is provided with a flange 31C which is adapted to rest on the shoulder 32C of the first piston member 31. Accordingly, when the upper end portion 32A of the second piston member 32 is pressed downward, the first piston member 31 is moved downward together with the second piston member 32 and when the upper end portion 31A of the first piston member 31 is pressed downward, only the first piston member 31 is moved downward. When the second pipette tip 52 is dipped in the control liquid after the upper end portion 32A of the second piston member 32 is pressed downward, and the upper end portion 32A is released, the control liquid is drawn into the second cylinder 22. By subsequently dipping the first pipette tip 51 in the liquid sample and releasing the upper end portion 51A of the first piston member 31, the sample liquid is drawn into the first cylinder 21. By pressing down the upper end portion 32A of the second piston member 32 after the control liquid and the liquid sample are thus drawn into the second and first cylinders 22 and 21, the two liquids can be discharged simultaneously and in the same amounts, and by pressing the upper end portions 31A and 32A in this order, the liquid sample is first discharged from the first tip 51 and then the control liquid is discharged from the second tip 52.

The longitudinal axes of the cylinders 21 and 22, and the piston members 31 and 32 are disposed to extend in parallel to each other in one plane. This arrangement is advantageous in that when the two piston members 31 and 32 are simultaneously pressed down, the upper end portions 31A and 32A can be engaged with each other in a good condition and the piston members 31 and 32 can be smoothly slid in the respective cylinders 21 and 22. When the part of each piston member which is not inserted into the cylinder is of flexible material, it is only necessary for the part of each piston member which is slid in the cylinder to be in parallel to the longitudinal axes of the cylinders 21 and 22 in one plane.

Figure 3A:
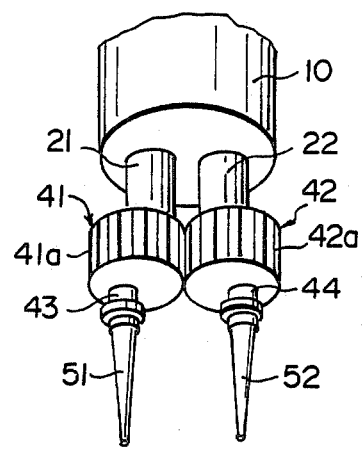
FIGS. 3A and 3B are fragmentary perspective views of a part of the pipette for illustrating the operation of the duplex pipette.
Figure 3B:
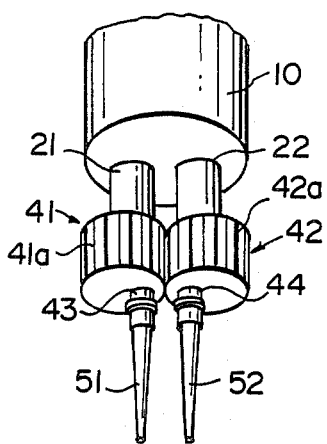

As shown in FIG. 3A, the first and second connecting members 41 and 42 are cylindrical members respectively mounted on the lower ends of the first and second cylinders 21 and 22 for rotation about the longitudinal axis of the corresponding cylinder. As illustrated in FIG. 2, the connecting members 41 and 42 have upwardly extending circular flanges coaxially inserted into the lower ends of cylinders 21 and 22, respectively. The connecting members 41 and 42 are respectively provided with tip mounting portions 43 and 44 eccentrically positioned on the lower surfaces thereof. The pipette tips 51 and 52 are respectively connected to the tip mounting portions 43 and 44. With this arrangement, the distance between the first and second pipette tips 51 and 52 can be changed by rotating the first and second connecting members 41 and 42 about the longitudinal axes of the corresponding cylinders 21 and 22 as shown in FIGS. 3A and 3B. In this particular embodiment, the connecting members 41 and 42 are provided with gear teeth 41a and 42a which are in mesh with each other so that both the connecting members 41 and 42 are rotated by rotating one of them. FIG. 3A shows the condition in which the distance between the first and second pipette tips 51 and 52 is the maximum, and FIG. 3B shows the condition in which the distance between the pipette tips 51 and 52 is minimum. It is preferred that the tip mounting portions 43 and 44 be arranged so that the longitudinal axis of each pipette tip extends in parallel to or in alignment with the longitudinal axis of the corresponding cylinder. This arrangement is advantageous in that the pipette tips 51 and 52 are prevented from accidentally interfering with each other and that the liquid sample and the control liquid are prevented from accidentally mixing with each other when the distance between the pipette tips 51 and 52 is narrowed. Further, calibration of the distance between the first and second pipette tips 51 and 52 can be easily and precisely made by this arrangement. If desired, the connecting members 41 and 42 are arranged so that only one of them is rotatable to change the distance between the tips 51 and 52.

Figure 4A:
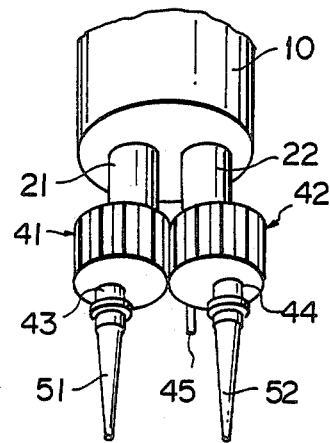
FIGS. 4A and 4B are views similar to FIGS. 3A and 3B but illustrating the operation of a duplex pipette in accordance with a modification of the pipette shown in FIG. 1.
Figure 4B:
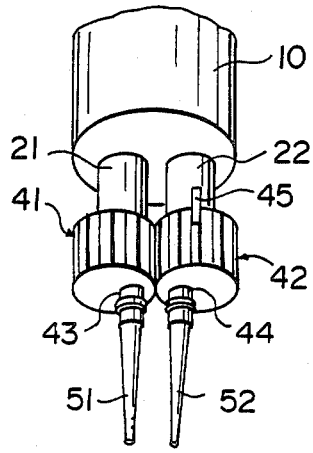

FIGS. 3A and 3B respectively show the conditions in which the distance between the pipette tips 51 and 52 is the maximum and the minimum. Setting the minimum distance between the pipette tips 51 and 52 to be equal to the center-to-center distance between the liquid deposition holes of the ionic activity measuring instrument is convenient for simultaneously depositing the liquid sample and the control liquid in the respective liquid deposition holes. It is preferred that a stopper or a click-stop mechanism (not shown) be provided to stop the connecting members 41 and 42 at a specific angular position, e.g., the angular position in which the distance between the tips 51 and 52 becomes equal to the center-to-center distance between the liquid deposition holes of the ionic activity measuring instrument or becomes maximum. Further, it is preferred that at least one of the connecting members 41 and 42 be provided with a scale indicating the distance between the tips 51 and 52. As shown in FIGS. 4A and 4B, by providing a lever 45 on one of the connecting members 41 and 42, the connecting members 41 and 42 can be easily rotated. Further, the lever 45 also functions as an indicator of the distance between the pipette tips 51 and 52. If desired, a pair of projections may be provided on the housing 10 to respectively abut against the lever 45 in positions corresponding to the maximum distance and the minimum distance between the tips 51 and 52. Further, it is possible to arrange an automatic control mechanism for automatically controlling the distance between the tips 51 and 52 to act on the lever 45 or the gear teeth 41a or 42a.

Though the tip mounting portions 43 and 44 are in the form of a tubular projection around which the dropping tip is fitted in this particular embodiment as shown in FIG. 2, they may be in the form of a circular groove into which the pipette tip is snugly fitted. It is preferred that the tip mounting portions be arranged so that the tips can be moved up and down by themselves or together with the mounting portions, whereby the distance between the distal ends of the pipette tips 51 and 52 and the portion on which the liquids held by the duplex pipette are to be deposited, e.g., the liquid deposition holes of the ionic activity measuring instrument, can be finely adjusted without moving the housing 10.

Figure 5A:
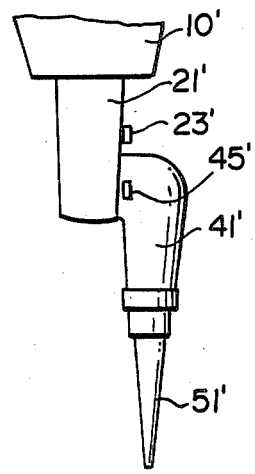
FIG. 5A is a fragmentary side view showing a part of a duplex pipette in accordance with another embodiment of the present invention.
Figure 5B:
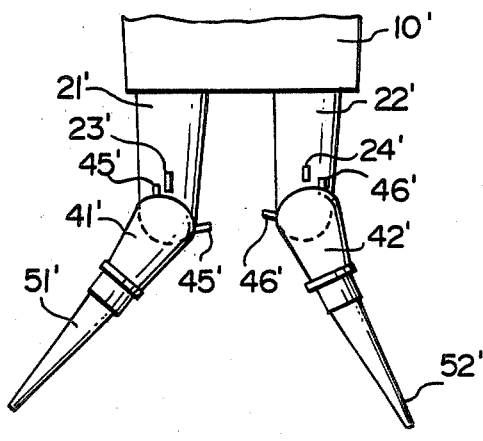
FIGS. 5B and 5C are fragmentary side views for illustrating the operation of the pipette of FIG. 5A.
Figure 5C:
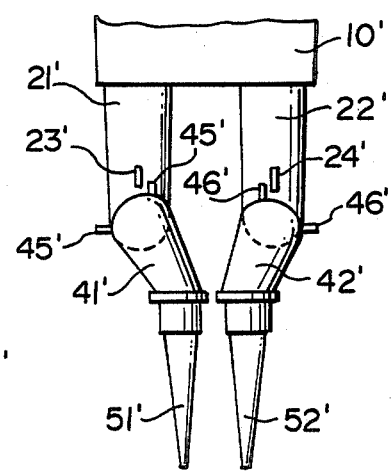

Another embodiment of the present invention will be described with reference to FIGS. 5A to 5C, hereinbelow.

The duplex pipette of this embodiment differs from that shown in FIGS. 1 to 3 mainly in the arrangement of the connecting members, and accordingly description will be made mainly on the arrangement of the connecting members. As shown in FIG. 5A (Though only the first connecting portion 41' is shown in FIG. 5A, the second connecting member 42' is of the same structure as the first connecting member 41' as can be understood from FIGS. 5B and 5C), the connecting member 41' is a leg-like member which is mounted for rotation on the lower side surface of the cylinder 21' at the upper end and on the lower end of which is mounted the pipette tip 51'. Cylinders 21' and 22' are attached to housing 10'.

The first connecting member 41' is provided with a pair of projections 45' angularly spaced from each other and the second connecting member 42' is provided with a pair of projections 46' angularly spaced from each other. The projections 45' and 46' are adapted to respectively abut against stoppers 23' and 24' provided on the cylinders 21' and 22'. That is, the connecting members 41' and 42' are rotatable between the positions in which the projections 45' and 46' respectively abut against the stoppers 23' and 24'. As can be understood from FIGS. 5B and 5C, the distance between the distal ends of the pipette tips 51' and 52' can be changed by rotating the connecting members 41' and 42'. That is, the distance between the tips can be enlarged by clockwisely rotating the first connecting member 41' and counterclockwisely rotating the second connecting member 42' as shown in FIG. 5B, and can be reduced by counterclockwisely rotating the first connecting member 41' and clockwisely rotating the second connecting member 42' as shown in FIG. 5C. The pipette tips 51' and 52' are mounted on the respective connecting members 41' and 42' to extend in parallel to the axes of the cylinders 21' and 22' when the distance between the tips 51' and 52' is minimized as shown in FIG. 5C.

Figure 6:
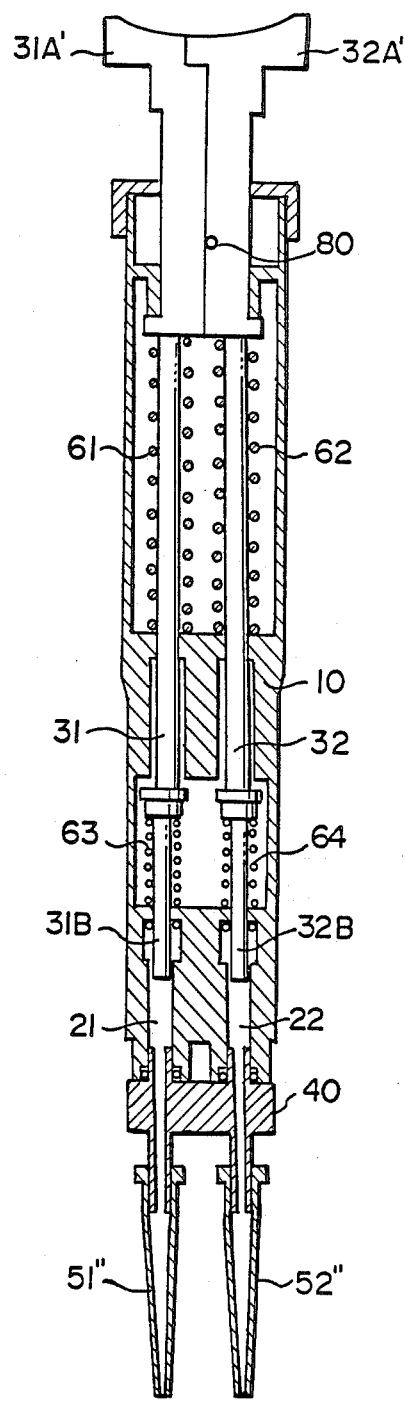
FIG. 6 is a cross-sectional view of a duplex pipette in accordance with still another embodiment of the present invention.

In still another embodiment of the present invention shown in FIG. 6, the pipette tips 51'' and 52'' are connected to the housing 10 by way of a single connecting member 40. The connecting member 40 is detachably connected to the housing 10 and is not arranged so that the distance between the tips 51'' and 52'' is variable. In this embodiment, by changing one connecting member for another which has a different distance between the tip mounting portions, the distance between the pipette tips can be changed. With this arrangement, the connecting member can be simplified in structure, whereby the manufacturing cost can be reduced and the possibility of occurrence of trouble such liquid leakage can be reduced. Further, in the embodiment shown in FIG. 6, the upper surfaces of the upper end portions 31A' and the 32A' are concaved to form a spherical surface, thereby facilitating manual operation of the piston members.

We claim:

1. A duplex pipette comprising a housing, first and second cylinders separately formed in the housing and fixedly spaced from one another, first and second piston members each having a lower end portion slidably received in the first and second cylinders, respectively, and a handle portion projecting outside the housing, and first and second pipette tips respectively mounted on the lower end of the first and second cylinders, respectively by means of first and second connecting members and being in a fluid communication with the corresponding cylinders, and first and second connecting means, the first connecting means connecting the first pipette tip to the first cylinder and the second connecting means connecting the second pipette tip to the second cylinder, the connecting means being constructed and arranged so that the distance between the pipette tips can be changed, wherein the pipette tips are each in communication with a corresponding one of said first and second cylinders by way of a first passage formed in the first connecting means and a second passage formed in the second connecting means.

2. A duplex pipette as defined in claim 1 in which said first and second cylinders extend substantially parallel to each other.

3. A duplex pipette as defined in claim 1 in which said first and second connecting means each comprises a cylindrical member which is mounted on the lower end of the cylinder corresponding thereto for rotation about a longitudinal axis of its corresponding cylinder, and each of said first and second pipette tips is eccentrically mounted on a lower surface of its respective one of said first and second cylindrical members.

4. A duplex pipette as defined in claim 3 in which each of said first and second pipette tips is mounted on its respective cylinder substantially parallel to the other of said first and second pipette tips.

* * * * *